United States Patent [19]

Kinoshita et al.

[11] 4,383,110
[45] May 10, 1983

[54] PROCESS FOR PURIFYING AND SEPARATING VITAMIN $B_{12}$

[75] Inventors: Tatsuo Kinoshita, Kawasaki; Yutaka Oguchi, Tokyo; Kenji Maruhashi, Yokohama; Ichiro Kojima, Yokosuka; Noboru Endoh, Tokyo; Tetsuo Satoh, Yokohama, all of Japan

[73] Assignee: Nippon Oil Company, Ltd., Tokyo, Japan

[21] Appl. No.: 324,633

[22] Filed: Nov. 24, 1981

[30] Foreign Application Priority Data

Nov. 29, 1980 [JP] Japan .................. 55-167374
Nov. 29, 1980 [JP] Japan .................. 55-167375

[51] Int. Cl.$^3$ ............................ C07H 15/12
[52] U.S. Cl. ............................ 536/28
[58] Field of Search ................... 536/28

[56] References Cited

PUBLICATIONS

The Merck Index, 9th Ed., Merck & Co., Inc., Rahway, N.J., 1976, pp. 1287-1288.

Primary Examiner—Nicky Chan
Attorney, Agent, or Firm—Wenderoth, Lind & Ponack

[57] ABSTRACT

A process for separating vitamin $B_{12}$ in pure form, which comprises bringing a vitamin $B_{12}$-containing liquid containing impurities into contact with a resin selected from the group consisting of (A) a divinylbenzene/styrene copolymer having a mode pore diameter of at least about 200 Å and a total pore volume of more than 0.6 ml/g, and (B) a copolymer of divinylbenzene/styrene/an unsaturated alkyl ester of an aromatic polycarboxylic acid represented by the formula

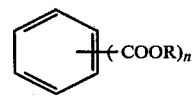

wherein R represents a $C_3$–$C_{10}$ unsaturated alkyl moiety having a carbon-carbon double bond and n is 2 or 3, said copolymer (B) having a surface area of at least about 700 m$^2$/g, to cause vitamin $B_{12}$ to be adsorbed to said resin, and eluting the vitamin $B_{12}$ with an eluent, and collecting the active eluate.

3 Claims, No Drawings

PROCESS FOR PURIFYING AND SEPARATING VITAMIN $B_{12}$

This invention relates to a process for separating vitamin $B_{12}$ in pure form from a vitamin $B_{12}$-containing liquid containing impurities, for example a vitamin $B_{12}$-containing liquid obtained by a fermentation method and a vitamin $B_{12}$-containing liquid obtained by a cellular extracting method. Specifically, it relates to a process for separating vitamin $B_{12}$ in pure form by which vitamin $B_{12}$ of high purity can be separated and recovered in a high yield at a high recovery ratio of, for example, more than about 98% and sometimes as high as 100%. This process is accomplished by simple and easy adsorbing and eluting operations and apparatus without the need for any additional operation such as additional purification or pre-purification while maintaining satisfactorily fast rates of adsorption and elution and good durability of the adsorbent.

More specifically, this invention pertains to a process for separating vitamin $B_{12}$ in pure form, which comprises bringing a vitamin $B_{12}$-containing liquid containing impurities into contact with a resin selected from the group consisting of (A) a divinylbenzene/styrene copolymer having a mode pore diameter of at least about 200 Å and a total pore volume of more than 0.6 ml/g, and (B) a copolymer of divinylbenzene/styrene/an unsaturated alkyl ester of an aromatic polycarboxylic acid represented by the formula

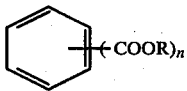

wherein R represents an unsaturated alkyl moiety of 3 to 10 carbon atoms having a carbon-carbon double bond and n is 2 or 3, said copolymer (B) having a surface area of at least about 700 m²/g, to cause vitamin $B_{12}$ to be adsorbed to said resin, and eluting the vitamin $B_{12}$ with an eluent, and collecting the active eluate.

It is known that vitamin $B_{12}$ is separated from a vitamin $B_{12}$-containing liquid containing impurities by an adsorption-elution operation using adsorbents such as activated carbon, activated alumina, Sephadex, and ion exchange resins. Such a method, however, has proved to be unsatisfactory in industrial practice because the amount of vitamin $B_{12}$ adsorbed to the adsorbents is small and the selective adsorbability of the adsorbents is low. Furthermore, the degree of purification of vitamin $B_{12}$ in the active fraction is low, and even by applying an additional purifying means, it is still difficult to separate vitamin $B_{12}$ in a satisfactory purity. Moreover, a purifying method which requires a combination of multiple steps has the defect that the loss of vitamin $B_{12}$ during the purifying process increases. The physical strength of the adsorbents used in such a method is also low. On repetition of the adsorption-elution operation, the adsorbents are liable to be blocked up, and the desired rate of flow cannot be maintained.

In an attempt to remedy these defects, there have been used methods for purifying crude vitamin $B_{12}$ by using Amberlite XAD-series resins (styrene/vinylbenzene resins made by Rohm & Haas Co.). But the use of resins of this type has also been found to be unsatisfactory.

Investigations of the present inventors have shown that the Amberlite XAD-series resins have a mode pore diameter of about 50 to 100 Å and a total pore volume of 0.3 to 0.6 ml/g but their capacity for adsorption of vitamin $B_{12}$ is not as high as is satisfactory. This defect is more pronounced with vitamin $B_{12}$-containing liquids containing relatively large amounts of impurities, such as a vitamin $B_{12}$-containing liquid obtained by a fermentation method and a vitamin $B_{12}$-containing liquid obtained by a cellular extracting method, showing a considerably reduced adsorptive power for these crude vitamin $B_{12}$-containing liquids. Furthermore, these resins are nonionic adsorptive resins having high porosity shown by their surface area of about 700 m²/g, but since the adsorptive surface of the resins is composed of hydrophobic or nonpolar molecules, it is presumably only the hydrophobic portion of vitamin $B_{12}$, having both a hydrophobic portion and a hydrophilic portion in its molecular structure, that participates in adsorption, and the above defect of the reduced adsorptive capacity is essentially difficult to remove.

The present inventors have made investigations in order to overcome the aforesaid technical problems associated with the separation of purified vitamin $B_{12}$ by an adsorbing-eluting technique from a vitamin $B_{12}$-containing liquid containing impurities, and to provide a process by which vitamin $B_{12}$ of high purity can be separated in a high yield with industrial advantage from a liquid containing crude vitamin $B_{12}$.

These investigations have led to the discovery that a resin selected from the group consisting of (A) a divinylbenzene/styrene copolymer having a mode pore diameter of at least 200 Å and a total pore volume of more than 0.6 ml/g and (B) a copolymer of divinylbenzene/styrene/an unsaturated alkyl ester of an aromatic polycarboxylic acid represented by the formula

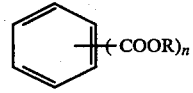

wherein R represents a $C_3$–$C_{10}$ unsaturated alkyl moiety having a carbon-carbon double bond and n is 2 or 3, said resin (B) having a surface area of at least about 700 m²/g, has an excellent ability to permit selective adsorption of a large amount of vitamin $B_{12}$ from a vitamin $B_{12}$-containing liquid containing impurities. Purified vitamin $B_{12}$ can be separated in a high recovery ratio of more than 98% and even 100% by simple and easy adsorption-elution operations and apparatus without the need for any additional purifying means and/or a preliminary purifying means.

It has also been found that with the specified resin adsorbent in accordance with this invention, a satisfactory adsorption-elution flow rate can be obtained in the treatment of a vitamin $B_{12}$-containing liquid containing impurities, and in repeated operations, the trouble of blocking up the resin adsorbent can be avoided. The resin exhibits high durability and can be advantageously lead to the improvement of the industrial practice of the purification and separation of vitamin $B_{12}$ from vitamin $B_{12}$-containing liquids containing impurities.

It has further been found in accordance with this invention that vitamin $B_{12}$ of high purity can be separated without the need for an additional purifying means and/or a preliminary purifying means at a high recovery ratio of more than 98% and sometimes 100%, in contrast to a vitamin $B_{12}$ recovery ratio of 75 to 90% by a known conventional recovery means using organic solvents such as phenol, or a vitamin $B_{12}$ recovery ratio of 63 to 95% by a known conventional adsorption-elution means by conventional adsorbents such as activated carbon, active alumina or ion-exchange resins. The resin in accordance with this invention retains the aforesaid excellent purifying and separating effect even in 100 cycles of a durability test.

It is an object of this invention therefore to provide an improved process for separating vitamin $B_{12}$ in pure form.

The above and other objects and advantages of this invention will become apparent from the following description.

The resin (A) used in the process of this invention is a divinylbenzene/styrene copolymer having a mode pore diameter of at least about 200 Å and a total pore volume of more than 0.6 ml/g. The adsorbent resin (A) which satisfies this mode pore diameter and total pore volume condition uniformly has a macroreticular structure and is highly porous, and exhibits about 2 to about 4 times as good an ability to adsorb vitamin $B_{12}$ as a previously used nonionic adsorbent resin such as Amberlite XAD-2.

The mode pore diameter is at least about 200 Å, preferably at least 250 Å, for example about 200 Å to 1200 Å, preferably 250 Å to 1200 Å, and the total pore volume is more than 0.6 ml/g, to about 1.2 ml/g, preferably 0.68 to 1.2 ml/g.

In addition to the above parameters, the resin (A) used in this invention should preferably meet the requirement that pores having a pore diameter of at least about 200 Å in it have a pore volume of at least 0.1 ml/g, preferably 0.2 to 1.0 ml/g.

The resin (B) used in the process of this invention is a copolymer of divinylbenzene/styrene/a saturated alkyl ester of an aromatic polycarboxylic acid having the aforesaid formula, and has a surface area of at least about 700 $m^2/g$. While the conventional Amberlite XAD-series resins have no polar surface, the resin (B) has a moderate polar surface derived from the unsaturated alkyl ester of the aromatic polycarboxylic acid. The resin (B) exhibits about 4 to about 8 times as good an ability to adsorb vitamin $B_{12}$ as the conventional resins. The surface area of the resin (B) is at least about 700 $m^2/g$, preferably at least about 800 $m^2/g$, for example about 700 to about 1200 $m^2/g$, preferably about 800 to about 1200 $m^2/g$.

The shape of the resins (A) and (B) used in this invention may be freely chosen. For example, they may be in the form of a powder, granule, pellets, etc.

The mode pore diameter and total pore volume of the resin (A) and the surface area of the resin (B) are measured by the following methods.

Each of the resins (A) and (B) are filled in a column having a diameter of 8 mm and a length of 500 mm, and a chloroform solution of each of 10 kinds of polystyrene having known molecule chain lengths and a chloroform solution of styrene are respectively passed through the resin-filled column. The volume of each polystyrene eluted Vi (ml) is measured.

Each polystyrene has a molecular chain length of from $10^4$ Å to $10^2$ Å and the molecular chain length distribution is very narrow.

By using the molecular chain length (A) and the elution volume Vi (ml) and the weight W (g) of a resin filled in a column, the total pore volume (V ml/g), the pore volume ($V_{200}$ ml/g) of pores having a pore diameter of at least about 200 Å and the surface area (S $m^2/g$) are calculated from the following equations.

| | | |
|---|---|---|
| (1) | Vi (ml/g) = | $(V_m - V_n)/W$ |
| (2) | Si ($m^2/g$) = | $8 \cdot Vi \cdot 10^4/(m + n)$ |
| (3) | V (ml/g) = | $\sum_{i=15}^{i=8000} Vi$ |
| (4) | $V_{200}$ (ml/g) = | $\sum_{i=200}^{i=8000} Vi$ |
| (5) | S ($m^2/g$) = | $\sum_{i=15}^{i=8000} Si$ |

Vi: the pore volume of mA to nA
Vm: the volume of polystyrene of mA eluted
Vn: the volume of polystyrene of nA eluted
Si: the surface area of mA to nA
m and n: molecular chain length The mode pore diameter is defined as a volume of (m+n)/2 at a maximum value of Vi in a histogram prepared by plotting Vi on the ordinate and (m+n)/2 on the abscissa.

The resins (A) and (B) used in the process of this invention can be produced by known suspension polymerization techniques in aqueous media. The resin (A) is available on the market under the tradenames of Diaion HP-10, HP-20, HP-30, HP-40 and HP-50 (products of Mitsubishi Chemical Co., Ltd.).

The resin (A) can be derived from divinylbenzene and styrene or its functional derivative. The resin (B) can be derived from divinylbenzene, styrene or its functional derivative, and the unsaturated alkyl ester of an aromatic polycarboxylic acid. Examples of the functional derivatives of styrene include alkyl-substituted derivatives having $C_1$–$C_6$ alkyl group, such as methylstyrene, ethylstyrene, dimethylstyrene and propylstyrene. Examples of the unsaturated alkyl ester of an aromatic polycarboxylic acid are di- or tri-$C_3$–$C_{10}$ alkenyl esters such as triisopropenyl 1,2,4-benzenetricarboxylate and diisopropenyl terephthalate. In forming the resin (B), one or more of styrene monomers selected from styrene and its functional derivatives, and one or more of the unsaturated alkyl esters of aromatic polycarboxylic acids can be used.

In the resin (A) or (B), the content of the styrene monomer or the unsaturated alkyl ester of an aromatic polycarboxylic acid can be properly selected and changed. The amount of the styrene monomer is preferably about 30 to about 80% by weight, especially preferably about 45 to about 70% by weight, based on the total amount of the styrene monomer and divinylbenzene. The amount of the unsaturated alkyl ester of an aromatic polycarboxylic acid is preferably up to about 30% by weight, more preferably about 0.1 to about 30% by weight, and especially preferably about 1 to about 10% by weight, based on the total amount of the divinylbenzene, the styrene monomer and the unsaturated alkyl ester of an aromatic polycarboxylic acid.

Commercially available divinylbenzene usually contains about 40 to about 70% by weight of m- and p-divinylbenzenes and about 30 to about 60% by weight of o-, m- and p-ethylstyrene. This commercial divinylbenzene can also be used as such as the aforesaid divinylbenzene and styrene monomer.

The copolymerization reaction can be performed in accordance with techniques known per se. For example, the resin (A) or (B) can be produced by copolymerizing in suspension divinylbenzene, and styrene or its functional derivative and further the unsaturated alkyl ester of an aromatic polycarboxylic acid in the presence of a polymerization initiator.

Known radical polymerization initiators soluble in the aforesaid monomers can be used in the above copolymerization reaction. Examples include benzoyl peroxide, lauroyl peroxide, tert-butyl peracetate, tertbutyl perpivalate, and azobisisobutyronitrile. The amount of the polymerization initiator can be properly chosen, and, for example, is about 0.1 to about 10% by weight, preferably about 0.5 to about 3% by weight.

Preferably, a dispersing agent is used in the aqueous suspension copolymerization in order to obtain a granular copolymer. Examples of such dispersing agents include difficultly soluble metal salts of inorganic acids such as barium sulfate, calcium carbonate and tricalcium phosphate; difficultly soluble clay minerals such as bentonite and clay; and natural or synthetic water-soluble polymeric materials such as starch, methyl cellulose, gelatin, polyvinyl alcohol, partially saponified polyvinyl alcohol, and polyacrylic acid salts such as poly(sodium acrylate) or poly(potassium acrylate). The amount of the dispersing agent can be properly selected, and, for example, is about 0.1 to about 10% by weight, preferably about 0.5 to about 7% by weight, based on the total amount of the monomeric mixture.

In performing the aqueous suspension copolymerization, a dispersion stabilizer can also be used. The disersion stabilizer may include, for example, sodium dodecylbenzenesulfonate and other various surface-active agent. The use of the dispersing agent with or without the dispersion stabilizer prevents the size increase of a gel caused by coalescing of the solvent and the monomers partly in the suspension polymerization, and makes it possible to easily form a copolymer of divinylbenzene/styrene or a copolymer of divinylbenzene/styrene/an unsaturated alkyl ester of an aromatic polycarboxylic acid having a uniform particle size. Furthermore, as a result, the particle size distribution of the resulting resin particles is improved, and resin particles (A) or resin particles (B) having an excellent ability to adsorb vitamin $B_{12}$ can be obtained.

If desired, a mixture of solvents which become good solvents for at least one of the divinylbenzene and the unsaturated alkyl esters of aromatic polycarboxylic acids can also be used.

Examples of such good solvents are alkyl-substituted benzenes such as diethylbenzene, trimethylbenzene and methylisopropylbenzene as good solvents for divinylbenzene; and aliphatic alcohols such as tert-isoamyl alcohol and tert-butylalcohol as good solvents for the unsaturated alkyl esters of aromatic polycarboxylic acids. For example, when a mixture of tert-isoamyl alcohol and diethylbenzene is used as a solvent, it acts as a good solvent for one of the monomers but as a poor solvent for the other monomer. Consequently, it serves to impart a macroreticular structure equally to the resulting resin particles and increase the porosity of the entire resin. This is effective for reducing the degree of swelling of the adsorbent resins used in this invention, and serves to impart better vitamin $B_{12}$ separating ability to the resins.

Preferably, the aqueous suspension copolymerization is carried out usually in an inert gas atmosphere such as nitrogen, and the copolymerization temperature and time can be selected properly depending upon the type of the polymerization initiator, etc. For example, a temperature of about 0° to about 110° C., preferably about 50° to about 100° C., and a period of about 8 hours to about 16 hours can be cited as examples.

According to the process of this invention, a vitamin $B_{12}$-containing liquid containing impurities is brought into contact with the resin (A) and/or the resin (B) to cause adsorption of vitamin $B_{12}$ to the resin. The vitamin $B_{12}$ is eluted with an eluent and the active eluate is collected. As a result, highly pure vitamin $B_{12}$ can be separated in a high yield by simple and easy adsorbing and eluting operations and apparatus without the need for an additional purifying means and/or a preliminary purifying means while maintaining satisfactorily fast rates of flow in adsorption and elution and excellent durability of the adsorbent resin.

The vitamin $B_{12}$-containing liquid containing impurities to be treated by adsorption and elution by the process of this invention is, for example, a crude vitamin $B_{12}$-containing liquid obtained by extracting vitamin $B_{12}$ accumulated in the culture broth or cultivated microbial cells which is obtained by cultivating a known vitamin $B_{12}$-producing microorganism in a nutrient medium, with water or an alcohol such as methanol, ethanol or isopropanol, a crude vitamin $B_{12}$-containing liquid obtained by destroying the cellular membranes of the vitamin $B_{12}$-containing cultivated microbial cells by milling and other mechanical means or ultrasonic means, or a crude vitamin $B_{12}$-containing liquid obtained by extracting with water or an alcohol the aforesaid crude vitamin $B_{12}$-containing liquid obtained by the cellular membrane destruction.

The production of vitamin $B_{12}$ by a fermentation method and the vitamin $B_{12}$-producing microorganisms are known, and can be used for the formation of the crude vitamin $B_{12}$-containing liquids to be treated by the process of this invention.

Examples of the known vitamin $B_{12}$-producing microorganism are microorganisms belonging to the genera Propionibacterium, Streptomyces, Arthrobacter, Corynebacterium, Rhodopseudomonas, Mycobacterium and Pseudomonas. Specific examples of these known microorganisms are shown below. They are available from the microorganism depositories indicated.

*Propionibacterium freudenreichii* (ATCC 6207),
*Propionibacterium shermanii* (ATCC 8262),
*Streptomyces olivaceus* (ATCC 3335),
*Arthrobacter hyalinus* (ATCC 31263),
*Arthrobacter simplex* (ATCC 6946),
*Rhodopseudomonas spheroides* (ATCC 11167),
*Rhodopseudomonas capsulata* (ATCC 11166),
Corynebacterium sp. (IFO 12320),
*Mycobacterium smegmatis* (IFO 3082), and
*Pseudomonas denitrificans* (ATCC 13867).

A process for producing vitamin $B_{12}$ by fermentation using known vitamin $B_{12}$-producing microorganisms as exemplified above is also known, and disclosed, for example, in Microbial Technology, 2nd edition, vol. 1, pages 497–519, 1979, Academic Press, Inc.

The process of this invention involves bringing the aforesaid crude vitamin $B_{12}$-containing liquid into contact with the resin adsorbent (A) and/or the resin adsorbent (B) to cause adsorption of vitamin $B_{12}$ to the resin, eluting the adsorbed vitamin $B_{12}$ from the resin with an eluent, and collecting the active eluate.

For the contacting step, any means which can permit full contact of the two can be used. For example, there can be used a batch method in which the adsorbent resin is mixed with the vitamin $B_{12}$-containing liquid, and if desired, the mixture is stirred to effect contact of both. There can also be employed a column chromatographic method which comprises filling the adsorbent resin in a suitable column, and passing the vitamin $B_{12}$-containing liquid through the filled resin layer. In the case of the batch method, the pH of the vitamin $B_{12}$-containing liquid is adjusted to a suitable value, for example about 5 to about 8, preferably about 7, and a suitable amount (for example about 1 to about 50 parts by volume per part by volume of the crude vitamin $B_{12}$-containing liquid) of the adsorbent is added. Then, the mixture is gently stirred for about 10 minutes to about 2 hours, usually for about 20 minutes to about 1 hour. The temperature used in the adsorption operation may be room temperature, but is as low as possible, for example about 10° to about 30° C. The column chromatographic method can also be performed by passing the vitamin $B_{12}$-containing liquid through a layer of the filled adsorbent under pH and temperature conditions similar to those shown in the case of the batch method.

After the adsorbing treatment, the resin is washed. Then, it is eluted with an eluent. For example, it is preferred that the resin which has adsorbed vitamin $B_{12}$ be washed with water or a hydrous alcohol having a low concentration such as 5% aqueous methanol, 2% aqueous ethanol or 1% aqueous isopropanol, and then eluted with an eluent.

By eluting vitamin $B_{12}$ from the adsorbent resin by means of an eluent, an active eluate which contains purified vitamin $B_{12}$ is obtained.

Ordinary eluents can be used, and examples include aqueous solutions of lower aliphatic alcohols, acids, alkalies and salts. Specific examples include lower aliphatic alcohols such as methanol, ethanol and isopropanol; acids, for example inorganic acids such as phosphoric acid, boric acid and hydrochloric acid and organic aliphatic carboxylic acids such as acetic acid; alkalies such as sodium hydroxide, monoammonium phosphate, diammonium phosphate and ammonium nitrate; and salts such as sodium carbonate, sodium acetate, sodium phosphate and potassium phosphate. The eluent can be properly selected also depending upon the types and amounts of impurities, and the type of the adsorbent resin. Aqueous solutions of lower aliphatic alcohols are preferred. For example, hydrous alcohols having an alcohol concentration of less than about 50%, such as 25 to 50% methanol, 15–40% ethanol, and 6–20% isopropanol, can be used.

The eluting operation can be carried out at room temperature, and heating or cooling is not particularly required. If desired, heating or cooling may be effected. For example, the eluting operation may be carried out at about 30° to about 80° C.

By the above procedure, the active eluate is obtained and if desired, concentrated, recrystallized, or otherwise worked up.

The following examples illustrate the present invention more specifically.

EXAMPLE 1

100 ml of a granular divinylbenzene/styrene copolymer having a mode pore diameter of 320 Å and total pore volume of 0.91 which was produced by an aqueous suspension polymerization technique using industrial divinylbenzene (purity about 55%, the remainder being ethylvinylbenzene) was filled in a glass column.

Pores having a pore diameter of at least about 200 Å in this resin had a pore volume of 0.50 ml/g.

A ground product of microbial cells containing vitamin $B_{12}$ obtained by centrifugally separating a culture broth of *Propionibacterium shermanii* (IFO 12391), a vitamin $B_{12}$-producing organism, was extracted with 80% aqueous ethanol containing KCN. The resulting vitamin $B_{12}$-containing liquid containing impurities was concentrated to 10 times, and water in an amount ten times as large as the concentrate was added to the concentrate to provide a liquid containing vitamin $B_{12}$ and impurities (vitamin $B_{12}$ content 23 ppm).

One liter of the vitamin $B_{12}$-containing liquid was allowed to flow down through the granular resin layer of the column at a flow rate of 4 ml/min. to cause it to be adsorbed to the resin. Continuously, 2 liters of deionized water was allowed to flow through the resin to cause impurities to flow into the adsorption waste liquid.

Then, 3 liters of 40% aqueous methanol was allowed to flow down through the column to elute vitamin $B_{12}$. The flow rate was 3 ml/min. One liter of the active eluate was collected, and the concentration of vitamin $B_{12}$ of the active eluate was measured by a microbiological assay method. It was found to be 23 ppm. Thus, the ratio of recovery of vitamin $B_{12}$ from the liquid containing vitamin $B_{12}$ and impurities was 100%.

EXAMPLE 2

100 ml of a commercial divinylbenzene/styrene copolymer (Diaion HP-20; mode pore diameter 460 Å, total pore volume 1.08 ml/g) was filled in a glass column, and 1 liter of the same liquid as in Example 1 containing vitamin $B_{12}$ and impurities (vitamin $B_{12}$ content 23 ppm) was charged onto the column and allowed to flow down through the resin layer at a flow rate of 4 ml/min. to cause adsorption of vitamin $B_{12}$. Continuously, 2 liters of deionized water was allowed to flow down through the column at a rate of 4 ml/min. to cause the impurities to flow into the waste liquid. Then, vitamin $B_{12}$ was diluted with 40% aqueous methanol. One liter of the active eluate was collected, and the concentration of vitamin $B_{12}$ was measured by a microbiological assay method. It was found to be 23 ppm as in Example 1. Thus, the ratio of recovery of vitamin $B_{12}$ from the vitamin $B_{12}$-containing liquid containing impurities was 100%.

EXAMPLE 3

A 150-liter stirred tank was charged with 5.0 kg of industrial divinylbenzene (purity about 55%; the remainder being ethylvinylbenzene), 1 kg of tripropenyl-1,2,4-benzenetricarboxylate, 6.0 kg of diethylbenzene, 3.0 kg of isoamyl alcohol, 80 kg of benzoyl peroxide, 100 liters of water, 4 kg of tricalcium phosphate and 6 g of sodium dodecylbenzenesulfonate, and with stirring, the mixture was subjected to suspension polymerization at 90° C. for 8 hours to form a granular crosslinked polymer.

The resulting granular polymer was filtered, washed with methanol and chloroform in a column and again filtered, and dried under reduced pressure at 60° to 80° C. to give 5.3 kg of a white non-transparent granular polymer.

The polymer had a surface area of 874 m$^2$/g and a total pore volume of 1.7 ml/g.

Pores having a pore diameter of at least about 200 Å in the resin had a pore volume of 0.30 ml/g.

This resin showed an infrared absorption at 1740 cm$^{-1}$ characteristic of the carbonyl group. This fact shows that tripropenyl 1,2,4-benzenetricarboxylate was effectively incorporated into the polymer by copolymerization.

A vitamin B$_{12}$-containing product obtained by cultivating *Propionibacterium shermanii* (IFO 12391), a vitamin B$_{12}$-producing microorganism, was centrifuged, and vitamin B$_{12}$ was extracted together with impurities from the separated microbial cells using 80% aqueous ethanol containing KCN. The resulting solution was concentrated to 10 times by an evaporating operation to prepare a crude vitamin B$_{12}$ culture liquor (vitamin B$_{12}$ content 500 ppm). 100 cc of the culture liquor was caused to flow through a column filled with 3 liters of the above resin particles at a rate of 200 cc/min. by an ascending method to cause adsorption of vitamin B$_{12}$. Continuously, 10 liters of a 1% aqueous solution of acetic acid was passed through the column to cause the impurities to flow into the waste liquid. Then, vitamin B$_{12}$ was eluted with 30% aqueous methanol, and 8,000 cc of the active eluate was collected and dried to obtain vitamin B$_{12}$ powder. The powdery vitamin B$_{12}$ had a purity of 80%. The yield of vitamin B$_{12}$ from the cultivation liquor to the eluate was 100%.

EXAMPLE 4

A 150-liter stirred tank was charged with 5.0 kg of industrial divinylbenzene (purity about 55%; the remainder being ethylvinylbenzene), 0.25 kg of tripropenyl 1,2,4-benzenetricarboxylate, 4.0 kg of diethylbenzene, 2.0 kg of isoamyl alcohol, 80 g of benzoyl peroxide, 100 liters of water, 4 kg of tricalcium phosphate and 45 g of polycarboxylic acid-type polymeric surface-active agent (Caribon-B, tradename), and with stirring, the mixture was subjected to suspension polymerization at 90° C. for 8 hours to obtain a granular crosslinked polymer.

The polymer was filtered, washed with methanol and chloroform in a column, again filtered, and dried at 60° to 80° C. under reduced pressure to give 4.9 kg of a white non-transparent granular polymer.

The polymer had a surface area of 905 m$^2$/g and a total pore volume of 1.6 ml/g.

Pores having a pore diameter of at least about 200 Å in the resin had a pore volume of 0.30 ml/g.

This resin was well affinitive with water by causing water to flow within a column, and thus a resin column for column chromatography can be easily made.

A vitamin B$_{12}$-containing product obtained by cultivating *Propionibacterium shermanii* (IFO 12391), a vitamin B$_{12}$-producing microorganism, was centrifuged, and vitamin B$_{12}$ together with impurities was extracted with 80% aqueous ethanol containing KCN from the separated microbial cells. The resulting solution was concentrated to 10 times by an evaporating operation to prepare a crude vitamin B$_{12}$ cultivation liquor (containing 500 ppm of vitamin B$_{12}$). 100 cc of this solution was passed through a column filled with 3 liters of the above resin particles at a rate of 200 cc/min, by an ascending method to cause adsorption of vitamin B$_{12}$. Continuously, 10 liters of a 1% aqueous solution of acetic acid was caused to flow through the column to cause the impurities to flow into the waste liquid.

Then, vitamin B$_{12}$ was eluted with 20% aqueous isopropanol. 6000 cc of the active eluate was collected and dried to obtain vitamin B$_{12}$ powder. The yield from the cultivation liquor to the eluate was 98%.

What we claim is:

1. A process for separating vitamin B$_{12}$ in pure form, which comprises bringing a vitamin B$_{12}$-containing liquid containing impurities into contact with a resin selected from the group consisting of (A) a divinylbenzene/styrene copolymer having a mode pore diameter of at least about 200 Å and a total pore volume of more than 0.6 ml/g, and (B) a copolymer of divinylbenzene/styrene/an unsaturated alkyl ester of an aromatic polycarboxylic acid represented by the formula

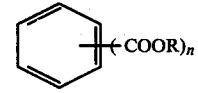

wherein R represents a C$_3$–C$_{10}$ unsaturated alkyl moiety having a carbon-carbon double bond and n is 2 or 3, said copolymer (B) having a surface area of at least about 700 m$^2$/g, to cause vitamin B$_{12}$ to be adsorbed to said resin, and eluting the vitamin B$_{12}$ with an eluent, and collecting the active eluate.

2. The process of claim 1 wherein the vitamin B$_{12}$-containing liquid has a pH of about 5 to about 8.

3. The process of claim 1 wherein the eluent is an aqueous solution containing a compound selected from the group consisting of lower aliphatic alcohols, acids, alkalies and salts.

* * * * *